United States Patent
Maggiano et al.

(10) Patent No.: US 9,538,917 B2
(45) Date of Patent: Jan. 10, 2017

(54) APPLANATION TONOMETER HAVING CORNEA ALIGNMENT MEANS

(71) Applicants: John M. Maggiano, Santa Ana, CA (US); Steven E. Maurath, Santa Ana, CA (US)

(72) Inventors: John M. Maggiano, Santa Ana, CA (US); Steven E. Maurath, Santa Ana, CA (US)

(73) Assignee: LightTouch, LLC, Carson City, NV (US)

( * ) Notice: Subject to any disclaimer, the term of this patent is extended or adjusted under 35 U.S.C. 154(b) by 163 days.

(21) Appl. No.: 14/451,063

(22) Filed: Aug. 4, 2014

(65) Prior Publication Data

US 2016/0029888 A1 Feb. 4, 2016

(51) Int. Cl.
*A61B 3/16* (2006.01)
*A61B 3/00* (2006.01)

(52) U.S. Cl.
CPC ............... *A61B 3/16* (2013.01); *A61B 3/0008* (2013.01); *A61B 3/0083* (2013.01)

(58) Field of Classification Search
None
See application file for complete search history.

(56) References Cited

U.S. PATENT DOCUMENTS

| | | | | |
|---|---|---|---|---|
| 4,875,767 | A * | 10/1989 | Wright | A61F 9/0136 351/205 |
| 5,190,042 | A * | 3/1993 | Hock | A61B 3/16 600/405 |
| 5,830,139 | A | 11/1998 | Abreu | |
| 2012/0108941 | A1* | 5/2012 | Maggiano | A61B 3/14 600/405 |
| 2015/0282981 | A1* | 10/2015 | Fuisz | A61F 9/0008 604/290 |

* cited by examiner

*Primary Examiner* — Devin Henson
*Assistant Examiner* — Matthew Kremer
(74) *Attorney, Agent, or Firm* — Morland C. Fischer

(57) ABSTRACT

An applanation tonometer is disclosed for providing a measurement of intraocular fluid pressure inside the eye of a patient. The applanation tonometer includes a light-transmitting prism having a cornea contact tip at one end and a cornea alignment aid at the opposite end. The cornea alignment aid enables the patient to advise a vision professional when a light source of the tonometer is properly aligned with his cornea so that intraocular fluid pressure can be accurately measured. A light-blocking baffle is located at the opposite end of the prism, and a thin light-transmitting channel is formed through the baffle to lie on the longitudinal axis of the prism. In a preferred embodiment, the light baffle is at least one opaque disk, and the light-transmitting channel is a clear spot at the center of the opaque disk through which light is transmitted to the patient's cornea.

6 Claims, 3 Drawing Sheets

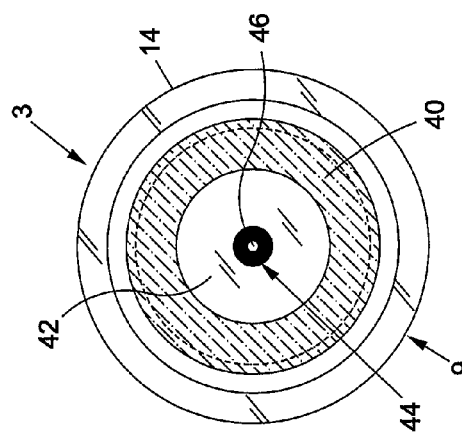
FIG. 6
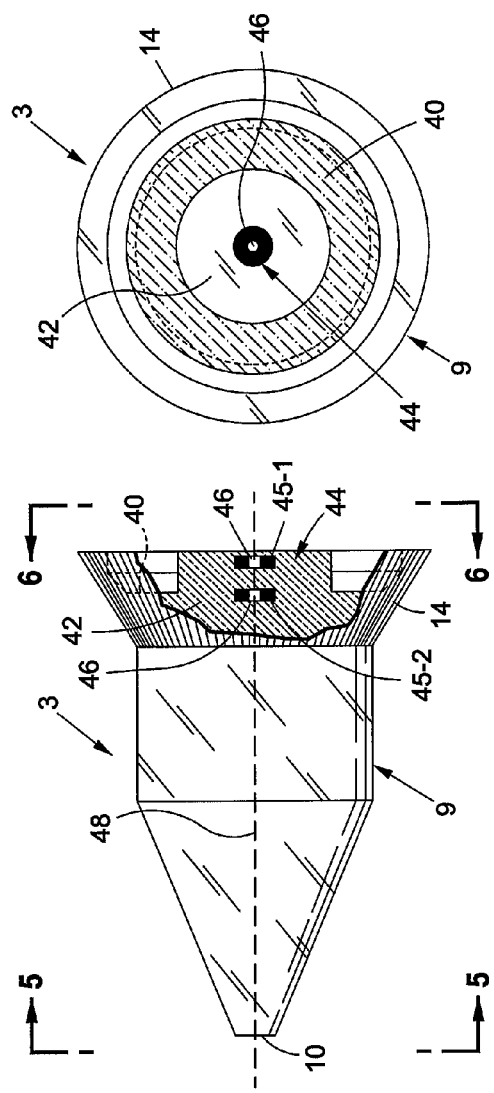
FIG. 3
FIG. 4
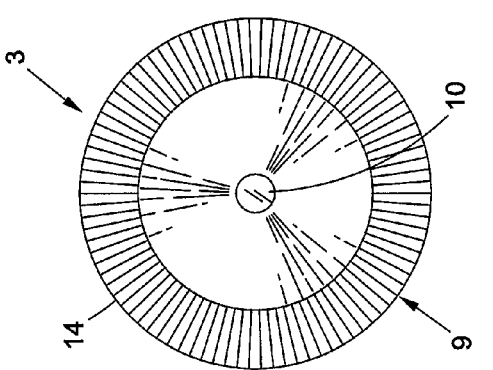
FIG. 5

APPLANATION TONOMETER HAVING CORNEA ALIGNMENT MEANS

BACKGROUND OF THE INVENTION

1. Field of the Invention

This invention relates to an applanation tonometer for providing a measurement of the intraocular fluid pressure inside the eye of a patient undergoing testing. The applanation tonometer includes cornea alignment means by which the patient is able to advise a vision professional when a light source of the tonometer is properly aligned with his cornea so that intraocular fluid pressure can be accurately measured while dwell time on the cornea and patient discomfort can be minimized.

2. Background Art

A tonometer is a non-invasive instrument which is used to measure pressure or tension in human or veterinary tissues. In the human body, intraocular fluid pressure in the eye (IOP) is measured to provide basic information for the diagnosis and treatment of glaucoma and related eye disease. Ease of application, accuracy of measurement and precise alignment of the tonometer between a (e.g., laser) light source and the patient's cornea are of paramount importance to obtaining reliable IOP measurements.

One example of an applanation tonometer that is adapted to make accurate IOP measurements is described in Patent Application Publication No. US 2012/0108941 published May 3, 2012. This applanation tonometer has a prism assembly at one end thereof, a light source module at the opposite end, and an intermediate beam splitter module located therebetween. The prism assembly includes a piezo element located adjacent a conical prism that tapers to a contact tip to be pressed against the patient's cornea to achieve applanation during the measurement of IOP. The light source module includes a laser or LED that supplies incoming light to the prism assembly to illuminate the patient's cornea. The beam splitter module includes a photo detector and an internal reflective surface that is aligned to reflect to the photo detector light which is reflected outwardly through the prism assembly before, during and after full applanation. The outputs of the piezo element and the photo detector provide force and area data pairs which are processed to provide a measurement of IOP.

It would be desirable to enhance the accuracy of the IOP measurements and minimize the time during which the measurements are made by being able to quickly and easily align the tonometer with respect to the patient's cornea, especially in cases where the patient moves his eye. To accomplish the foregoing, what would be advantageous is an alignment tool for use with the applanation tonometer by which to enable the patient to determine when the light source module and the prism module of the tonometer are ideally aligned with respect to his cornea so that the tonometer can be moved towards and into contact therewith.

SUMMARY OF THE INVENTION

In general terms, an applanation tonometer is disclosed by which to measure the intraocular fluid pressure (IOP) inside a human eye in order to make information available for the diagnosis and treatment of glaucoma and other ocular health issues. The applanation tonometer includes a prism assembly at one end thereof, a light source at the opposite end, and an intermediate beam splitter module located between the prism assembly and the laser module. The prism assembly of the applanation tonometer includes a pressure-responsive piezo element and a conical light-transmitting prism that tapers to a (e.g., circular) contact tip at the front to be pressed against the cornea. Lying opposite the contact tip at the rear of the prism is a cornea alignment means that enables the tonometer to be properly aligned so that the cornea is illuminated by light supplied from the light source via the light-transmitting prism of the prism assembly.

More particularly, and according to a preferred embodiment, an opaque (e.g., black paint or plastic) peripheral ring lies against the rear of the prism. The opaque peripheral ring surrounds a clear, light-transmitting area through the prism. A disk-like light baffle is located at the center of the light-transmitting area to block incident light directed towards the baffle by way of the light source and the beam splitter module. The sizes (i.e., diameters) of the light baffle at the rear of the prism and the contact tip at the front of the prism are preferably identical.

The aforementioned cornea alignment means includes a light-transmitting channel that runs through the center of the light baffle so as to lie on the longitudinal axis of the prism assembly, whereby the light-transmitting channel is axially aligned with the contact tip at the front of the prism. The light-transmitting channel can simply be a clear spot surrounded by the disk-like light baffle. In the alternative, the light baffle may be a pair of light-blocking disks that are spaced one above the other within the prism. In this case, each light-blocking disk has a clear spot at the center thereof, such that the respective clear spots of the disks lie on the longitudinal axis of the prism assembly. Accordingly, when the contact tip of the prism is positioned adjacent the cornea of a patient, light that is generated by the light source of the tonometer is transmitted down the light transmitting channel through the light baffle to the contact tip. When the patient sees a bright spot of light (corresponding in size to the light-transmitting channel), a visual indication is provided to the patient that the tonometer is properly aligned with respect to his cornea so that a measurement of IOP can now be made. However, should the patient otherwise see diffused light, a visual indication is provided to the patient that the tonometer is out of its ideal alignment with the cornea so that a position adjustment should first be made. In either case, the patient can alert the vision professional whether to accept or change the alignment of the tonometer and the position of the contact tip of the prism of the prism assembly with respect to the cornea of his eye. By virtue of being able to precisely align the applanation tonometer and its light source with the cornea, IOP can be efficiently and accurately measured while dwell time on the cornea and patient discomfort can be advantageously minimized.

BRIEF DESCRIPTION OF THE DRAWINGS

FIG. 3 is a perspective view of a prism assembly of the applanation tonometer of FIG. 1 to illustrate details of the cornea alignment means;

FIG. 4 is a side view, in partial cross-section, of the prism assembly shown in FIG. 3;

FIG. 5 is a front view of the prism assembly taken along lines 5-5 of FIG. 4;

FIG. 6 is a rear view of the prism assembly taken along lines 6-6 of FIG. 4;

DESCRIPTION OF THE PREFERRED EMBODIMENT

Turning to the drawings, an alignment means is described to enable a light source of an applanation tonometer to be precisely aligned with the cornea of a patient so that intraocular fluid pressure (IOP) of the patient's eye can be accurately measured. As will soon be explained, the applanation tonometer alignment means of this invention provides the patient undergoing testing with a visual indication of the alignment of the tonometer with the cornea of his eye prior to IOP measurement. In this manner, the patient can instruct the vision professional whether to accept or adjust the position of the tonometer relative to his cornea so that IOP measurement can then be completed within a minimal testing period with minimal dwell time on the cornea and with minimal patient discomfort.

The cornea alignment means herein disclosed has particular application with the applanation tonometer described in Patent Application Publication No. US 2012/0108941 entitled APPLANATION TONOMETER AND METHOD FOR MEASURING THE INTRAOCULAR PRESSURE OF THE EYE. Therefore, the details of this publication are incorporated herein by reference. However, it is to be understood that the use of the alignment means is not limited exclusively to the aforementioned tonometer.

Figure 1:
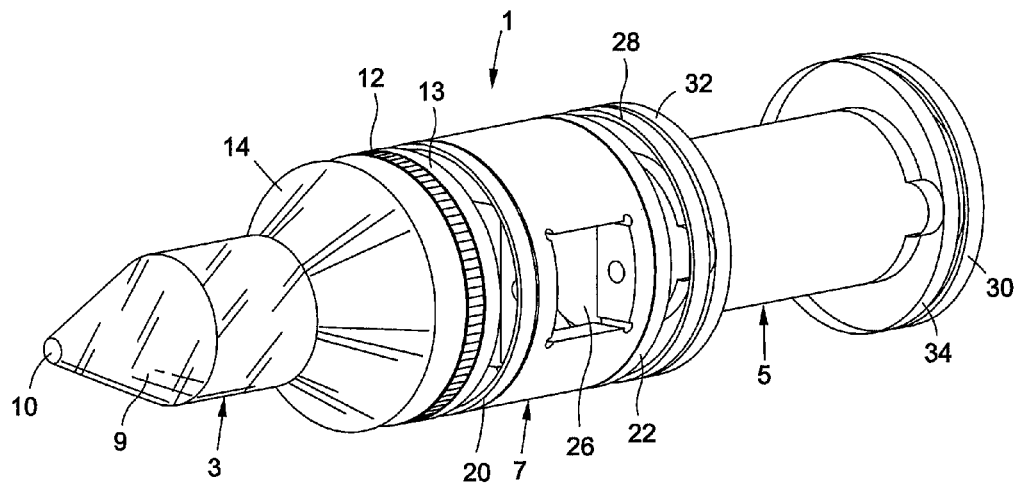
FIG. 1 is a perspective view of an applanation tonometer for measuring intraocular pressure (IOP) and including cornea alignment means according to a preferred embodiment of this invention whereby the tonometer can be properly aligned with the cornea prior to IOP measurement.
Figure 2:
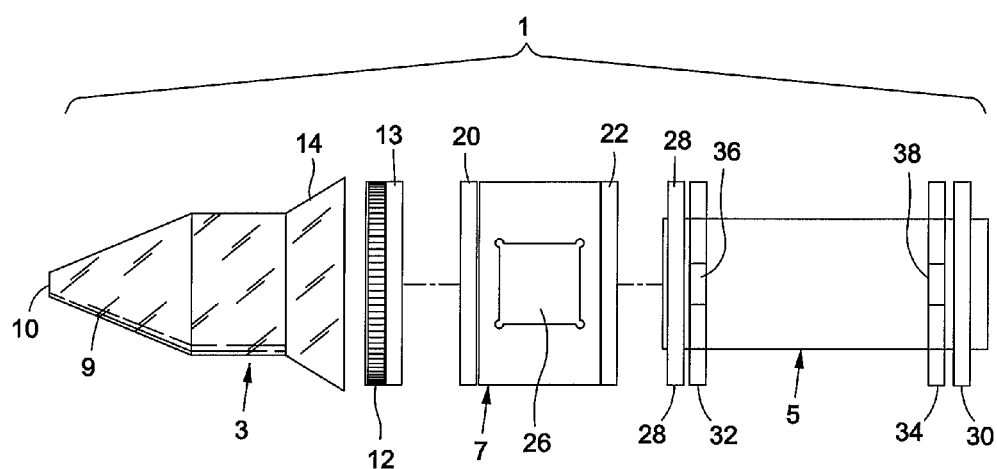
FIG. 2 is an exploded view of the applanation tonometer having the cornea alignment means shown in FIG. 1.

In this regard, FIGS. 1 and 2 of the drawings illustrate an applanation tonometer 1 that is adapted to provide a measurement of the IOP inside the eye of a patient being tested. Briefly, the applanation tonometer 1 includes a prism assembly 3 at one end thereof, a light source module 5 at the opposite end, and an intermediate beam splitter module 7 lying therebetween. The prism assembly 3, beam splitter module 7 and light source module 5 are axially aligned with one another.

The prism assembly 3 of the applanation tonometer 1 includes a light-transmitting prism 9 that is manufactured from glass, optically-clear cast acrylic, or any other suitable light-transmitting material. The proximal end of the prism 9 is preferably conical. The front of prism 9 is ground flat at the narrow end thereof to create a circular contact tip 10 to be moved into contact with the cornea of the eye of the patient being tested. The opposite distal end of prism 9 is cylindrical to provide a wide light transmission area between the light source module 5 and the contact tip 10. A piezo ring 12 lies adjacent the distal end of prism 9 to surround and position a force-responsive (i.e., piezo) element (designated 50 in FIG. 8) in alignment with the contact tip 10 of prism 9. A retainer ring 13 is located behind the prism 9 and piezo ring 12 to hold the piezo element against the prism assembly 3.

The light source module 5 preferably includes a Class II laser (e.g., a laser diode) that is adapted to supply incoming parallel-aligned laser light beams to the prism assembly 3 by way of the beam splitter module 7. The beam splitter module 7 includes a conventional beam splitter having an internal reflecting surface (designated 52 in FIG. 8) which is aligned with a photo detector, such as a photo diode (designated 54 in FIG. 8) to which outgoing light beams from the prism assembly 3 are reflected.

The prism assembly 3 also includes a flared hood 14 (best shown in FIGS. 3-6) that extends outwardly from the cylindrical distal end of prism 9. The flared hood 14 is sized and positioned relative to the piezo ring 12 to transmit a compressive pushing force that is generated when the contact tip 10 of the prism 9 contacts the patient's eye to the force-responsive piezo element that is surrounded by the ring 12. Retainer rings 20 and 22 surround opposite sides of the beam splitter module 7 to provide support thereto. A cavity 26 extends radially into the beam splitter module 7 in which to receive the aforementioned photo diode (54 in FIG. 8) so that the prism assembly 3 and photo diode can be positioned in optical alignment.

Retainer rings 28 and 30 surround and support opposite ends of the light source module 5. The light source module 5 also has alignment rings 32 and 34 lying inside and adjacent the retainer rings 28 and 30 to provide self-centering of the light source module 5 with respect to the beam splitter module 7 and the prism assembly 3. Wire ports 36 and 38 are formed in the alignment rings 32 and 34 through which electrical wires (not shown) are connected to the piezo element 50 of the prism assembly 3 and the photo diode 54 carried by the intermediate beam splitter module 7. The light source module 5 ideally provides parallel laser light beams to the prism 9 of the prism assembly 3 to be internally reflected by the prism 9 first to the beam splitter module 7 and then to the photo diode of the beam splitter module 7.

The applanation tonometer 1 also includes a pair of conventional light beam expanders and/or collimators 56 and 58 (best shown in FIG. 8) that is located between the prism assembly 3 and the beam splitter module 7 so as to lie in the paths of the incoming light transmitted from the light source module 5 and outgoing light reflected from the prism 9 so as to focus and absorb stray light and thereby reduce spurious light transmissions. Located between the beam splitter module 7 and the light source module 5 are another pair of conventional light beam expanders and/or collimators 60 and 62 (also best shown in FIG. 8). The expanders/collimators 60 and 62 may be identical to those designated 56 and 58 between the prism assembly 3 and beam splitter module 7. The light beam expanders and collimators 60 and 62 also control the incoming light and further ensure that parallel light beams will pass through the beam splitter module 7 to the prism assembly 3. In this regard, it may be appreciated that the pairs of light beam expanders/collimators 56, 58 and 60, 62 located at opposite ends of the beam splitter module 7 cooperate to form a well-known light management assembly.

Details of the light-transmitting prism assembly 3 of the applanation tonometer 1 are now provided while referring to FIGS. 3-6 of the drawings. As previously explained, the contact tip 10 of the conical proximal end of the prism 9 of prism assembly 3 is moved towards and against the patient's cornea during the measurement of IOP. Located inside the flared hood 14 at the rear of the distal cylindrical end of prism 9 opposite the contact tip 10 is an opaque light-blocking peripheral ring 40. The opaque peripheral ring 40 can be created by covering or coating the rear of the prism 9 with black paint or plastic. The opaque peripheral ring 40 surrounds a clear, light-transmitting area 42 of the prism 9. In FIGS. 3-6, the light-transmitting area 42 is shown including a cylindrical extension that stands outwardly from the prism 9 inside the opaque peripheral ring 40. However, the cylindrical shape of the light-transmitting area 42 is primarily to facilitate manufacturing, and it is to be understood that the light-transmitting area 42 may also lie flat inside the opaque peripheral ring 40 at the rear of prism 9.

A (e.g., round) light baffle 44 is located at the center of the light-transmitting area 42 at the rear of prism 9 to block incident light transmitted thereto by way of the light source module 5 and the beam splitter module 7. The shape and size (i.e., diameter) of the light baffle 44 at the rear of the prism 9 and the contact tip 10 at the front of the prism 9 are preferably identical. The light baffle 44 can be manufactured from an optically-opaque (i.e., light absorbing) or a light reflecting (e.g., polished) material. Or, like the opaque peripheral ring 40, the light baffle 44 can be a black paint or plastic covering or coating.

In a preferred embodiment, the light baffle 44 includes one or more opaque disks. In the example of FIGS. 3-6, the light baffle 44 is a pair of disks 45-1 and 45-2 that are spaced one above the other at the rear of the prism 9. That is, one or both of the pair of opaque disks 45-1 and 45-2 can be located above, against and/or embedded within the rear of prism 9.

As an important detail of the cornea alignment means of this invention, a hollow light-transmitting channel 46 runs through the light baffle 44. The light-transmitting channel 46 has an ideal diameter of 0.01-0.25 mm. As is best shown in FIG. 4, the light-transmitting channel 46 through light baffle 44 lies on the longitudinal axis of the prism assembly 3 such that channel 46 through baffle 44 at the distal end of the light-transmitting prism 9 and the contact tip 10 at the proximal end of prism 9 are axially aligned with one another. Thus, a light transmission path 48 is created along the longitudinal axis of the prism assembly 3 between the light-transmitting channel 46 through the light baffle 44 of prism 9 and the contact tip 10 thereof. In the example shown in FIGS. 3-6, the light-transmitting channel 46 through light baffle 44 includes a clear light-transmitting spot that is located at the center of and surrounded by each of the pair of opaque disks 45-1 and 45-2.

As previously described, in order to measure IOP, the contact tip 10 of the light-transmitting prism 9 is moved towards and pressed against the cornea of the patient undergoing testing so that the patient's cornea is illuminated with light supplied from the light source module (designated 5 in FIGS. 1 and 2). To be able to accurately measure IOP, the light source module 5 of the applanation tonometer must be initially aligned with the cornea, especially in cases where the patient moves his eye prior to testing.

Figure 7:
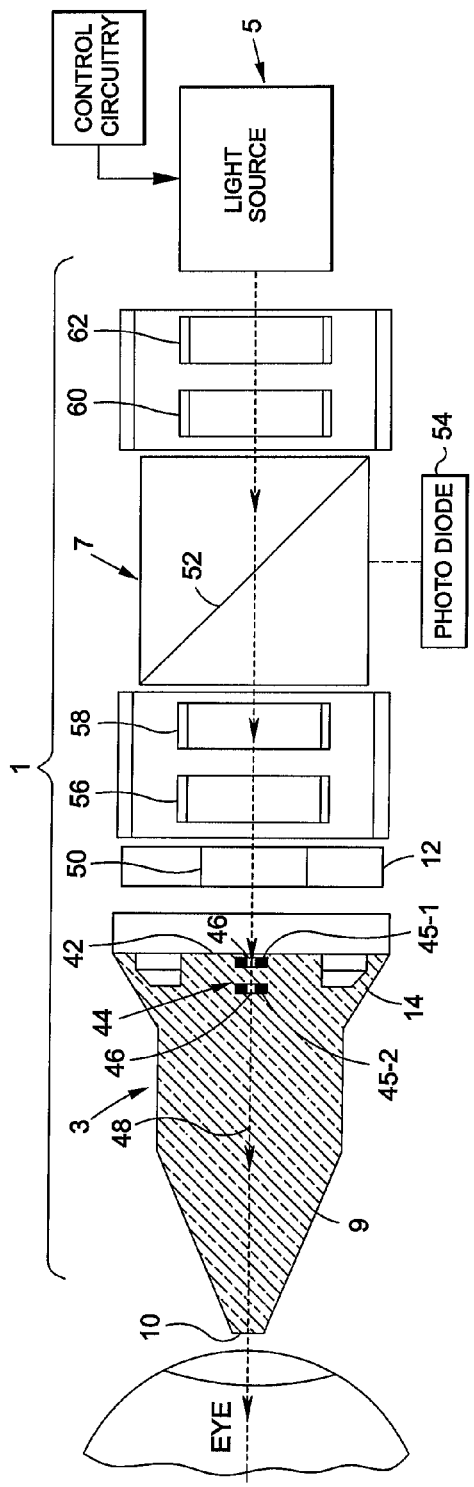
FIG. 7 illustrates the cornea alignment means being used to enable a light source of the applanation tonometer to be properly aligned to illuminate the cornea by way of the prism assembly so that a contact tip of the prism assembly can be moved into contact with the cornea to measure IOP.

As is best shown in FIG. 7 of the drawings, when the prism 9 is held adjacent to and spaced from the patient's cornea, light generated by the light source module 5 is transmitted down the light-transmitting channel 46 which runs through the light-transmitting spots at the centers of the opaque disks 45-1 and 45-2 of the baffle 44, along the light-transmitting path 48 of prism assembly 3, and finally to the patient's cornea via the contact tip 10 of prism 9. Should the patient see a bright spot of light (corresponding in size to the light-transmitting channel 46), a visual indication is provided to the patient that the applanation tonometer 1 and its light source module 5 are properly aligned with his cornea to enable an accurate measurement of IOP. However, should the patient otherwise see diffused light, a visual indication is provided to the patient that the tonometer and its light source module are out of an ideal alignment with the cornea. In this case, the patient can alert the vision professional (depending upon the clarity of the light spot visible to the patient through the contact tip 10 of prism 9) whether the position of the tonometer with respect to his cornea is acceptable for IOP measurement or first in need of adjustment prior to IOP measurement.

In other words, oral information provided by the patient allows the vision professional to quickly and easily identify the precise alignment of the applanation tonometer 1 and its light source module 5 with the patient's cornea so that IOP can then be accurately measured. By virtue of the foregoing, the time during which the testing is conducted, the dwell time on the patient's cornea and patient discomfort can all be advantageously minimized.

Once the applanation tonometer 1 of FIGS. 1 and 2 has been properly positioned in the manner just disclosed, the tonometer is used to measure IOP. In this regard, one method by which the applanation tonometer 1 can be used to measure IOP is identical to that described in the aforementioned Application Publication No. US 2012/0108941. Therefore, only a brief description of this method will be explained below.

Figure 8:
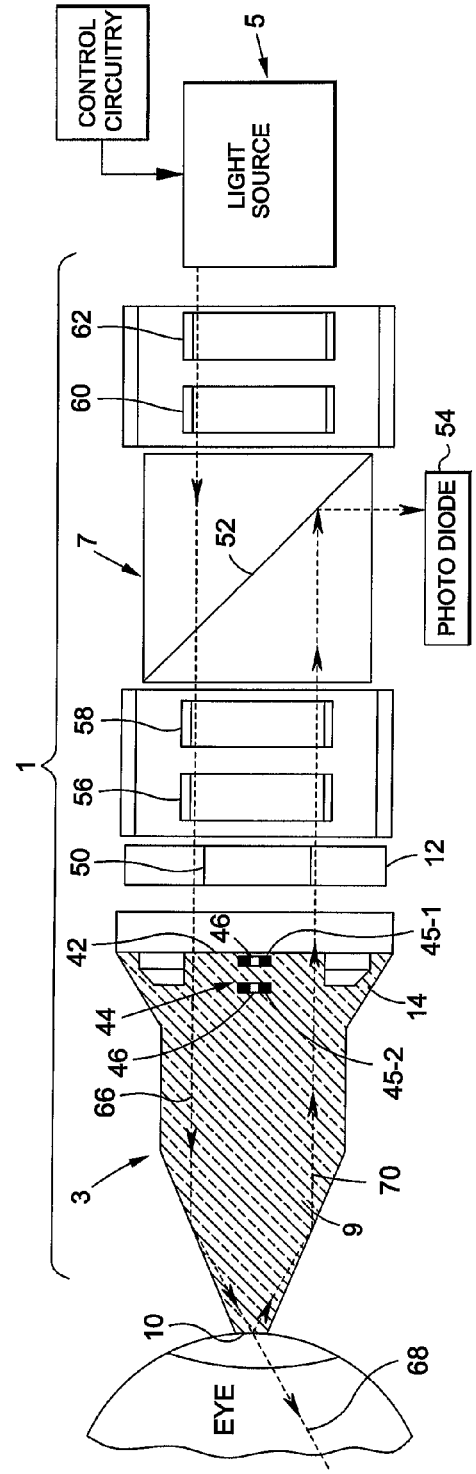
FIG. 8 illustrates the paths of incoming and reflected light beams through the applanation tonometer after the contact tip of the prism assembly has been moved into contact with the eye to achieve applanation during the measurement of IOP.

FIG. 8 of the drawings shows the applanation tonometer 1 after the contact tip 10 of the prism 9 of the prism assembly 3 has first been properly aligned with and then moved into full contact (i.e., applanation) with the cornea of the patient's eye. Incoming light 66 is transmitted from the light (e.g., laser) source module 5 and through the light-transmitting area 42 of the prism 9 located between the opaque peripheral ring 40 and the light baffle 44.

With the contact tip 10 of prism 9 pressed into contact against the patient's cornea to achieve full applanation, as shown, some of the light is decoupled from the incoming light 66 that is transmitted from the light source module 5 inwardly through the prism. The incoming light which is decoupled (designated 68) is transmitted through the contact tip 10 of the prism 9 and lost into the eye. The remaining light 70 which is not decoupled is reflected internally and outwardly through the prism 9 so as to reflect off the reflecting surface 52 of the beam splitter module 7 to be detected by the photo diode 54. Light (not shown in FIG. 8) during IOP testing is also transmitted and reflected along the light-transmitting path 48 of the prism assembly 3 shown in FIG. 7. The outputs of the force-responsive piezo element 50 and the photo diode 54 provide force and contact area data pairs which are processed to provide a measurement of IOP.

The invention claimed is:

1. An applanation tonometer to measure an intraocular pressure of an eye of a patient undergoing testing, said applanation tonometer comprising:

a light source to generate light, said light source to be aligned with a cornea of the patient's eye undergoing testing;

a light-transmitting body having first and opposite ends, a longitudinal axis running between said first and opposite ends, and a circular contact tip located at the first end to be moved into contact with an area of the eye undergoing testing and apply a pressure thereagainst, said circular contact tip being positioned to receive the light generated by said light source and transmitted in a first direction inwardly through said light-transmitting body towards the patient's eye and to reflect at least some of the inwardly-transmitted light in a second direction outwardly through said light-transmitting body away from the patient's eye depending upon the area of contact between the circular contact tip of said light-transmitting body and the patient's eye;

a pair of circular light-blocking disks spaced one behind the other and embedded within the opposite end of said light-transmitting body, each of said pair of circular light-blocking disks having a diameter which is identical to one another and to the diameter of the circular contact tip of said light transmitting body and a light-transmitting channel running through a center thereof and lying along the longitudinal axis of said light-transmitting body so that the light that is generated by said light source is transmitted from said light source in said first direction through the light-transmitting channels of said pair of circular light-blocking disks located at the opposite end of said light-transmitting body to the circular contact tip located at the first end of said light-transmitting body by which the cornea of the eye undergoing testing is illuminated, such that the light with which the cornea is illuminated provides a visual indication to the patient whether said light source and the patient's cornea are aligned with one another to enable the intraocular pressure of the patient's eye to be measured;

a photo detector to receive the light reflected by said circular contact tip in the second direction outwardly through said light-transmitting body and to provide an output signal in response thereto; and a force detector to provide an output signal in response to the pressure generated at the area of contact between the circular contact tip of said light-transmitting body and the patient's eye.

2. The applanation tonometer recited in claim 1, wherein the first end of said light-transmitting body is a prism having first and opposite ends, said prism being tapered between said first and opposite ends hereof to form said circular contact tip to be moved into contact with the patient's eye undergoing testing.

3. The applanation tonometer recited in claim 1, wherein each of said pair of circular light-blocking disks is opaque.

4. The applanation tonometer recited in claim 1, wherein each of said pair of circular light-blocking disks is reflective.

5. The applanation tonometer recited in claim 1, wherein the light-transmitting channel running through the center of each of said pair of circular light-blocking disks is a clear spot.

6. The applanation tonometer recited in claim 1, further comprising a flared hood extending outwardly from the opposite end of said light-transmitting body so as to surround said pair of circular light-blocking disks, said flared hood being positioned between said force detector and the circular contact tip at the first end of said light-transmitting body to provide a compressive force from said circular contact tip to said force detector when said circular contact tip is moved into contact with the patient's eye undergoing testing.

* * * * *